United States Patent [19]
Luce et al.

[11] Patent Number: 5,471,260
[45] Date of Patent: Nov. 28, 1995

[54] JOYSTICK FOR AN OPHTHALMIC INSTRUMENT WHERE VERTICAL MOVEMENT IS CONTROLLED BY ROTATING THE JOYSTICK

[75] Inventors: David A. Luce, Clarence Center; Joseph L. Zelvin, Larchmont, both of N.Y.

[73] Assignee: Leica Inc., Depew, N.Y.

[21] Appl. No.: 331,016

[22] Filed: Oct. 28, 1994

[51] Int. Cl.⁶ ........................................ A61B 3/10
[52] U.S. Cl. ........................................ 351/205; 351/245
[58] Field of Search .................................. 351/205, 206, 351/208, 209, 210, 211, 212, 227, 245

[56] References Cited

U.S. PATENT DOCUMENTS

| | | | |
|---|---|---|---|
| 4,165,924 | 8/1979 | Mohrman | 351/245 |
| 4,456,348 | 6/1984 | Schulz et al. | 351/212 |
| 5,404,184 | 4/1995 | Koike et al. | 351/205 |

FOREIGN PATENT DOCUMENTS 4-50562 of 1992 Japan.

*Primary Examiner*—William L. Sikes
*Assistant Examiner*—James A. Dudek
*Attorney, Agent, or Firm*—Bean, Kauffman & Spencer

[57] ABSTRACT

The disclosure relates to a joystick for positioning a test axis of an ophthalmic instrument relative to an eye of a patient. In a preferred embodiment, the joystick includes an actuator extending therefrom and arranged to alternately engage a pair of motor control switches incident to slight rotation of the joystick in opposite directions, thereby activating a motor drive to raise and lower the test axis.

8 Claims, 3 Drawing Sheets

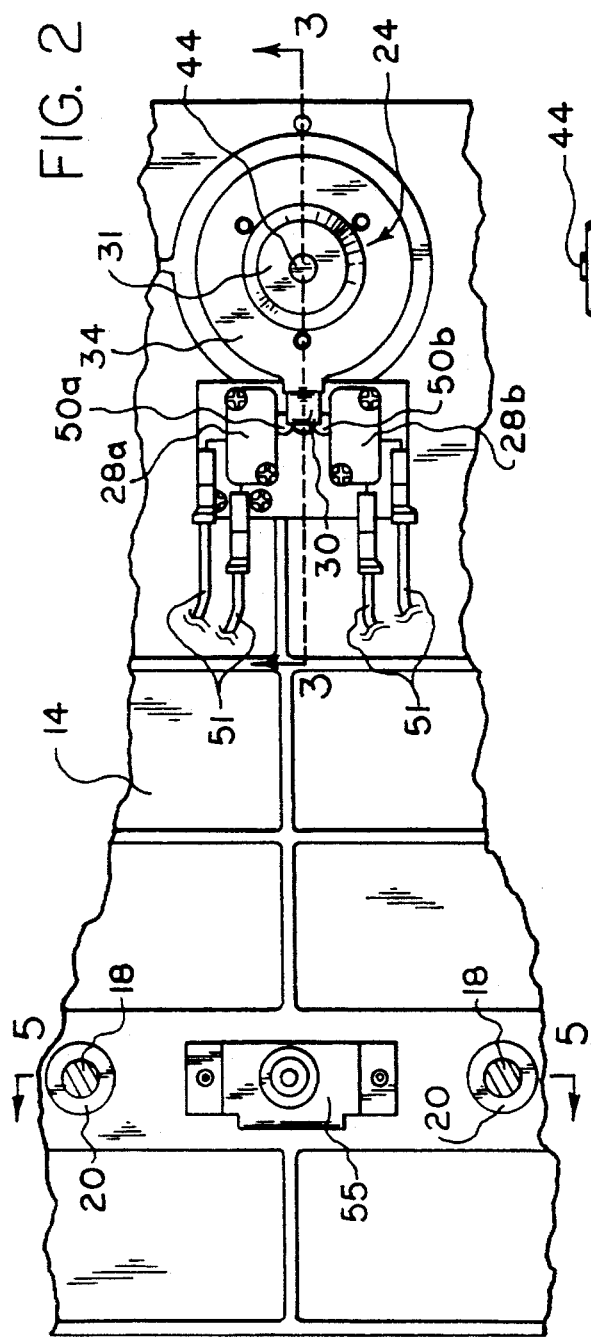
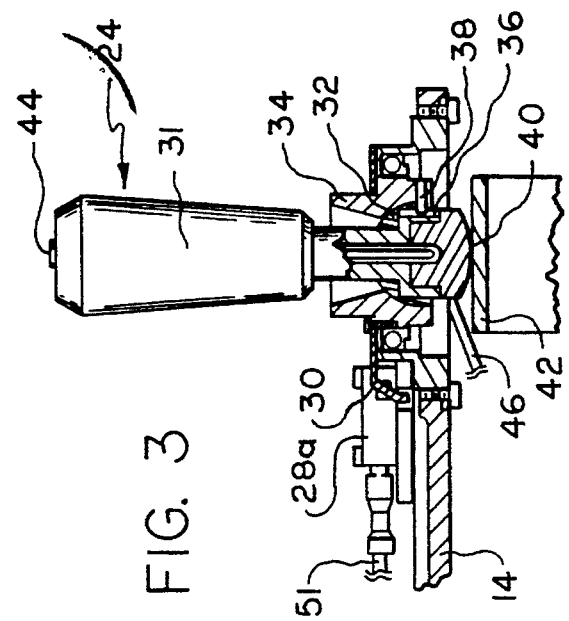
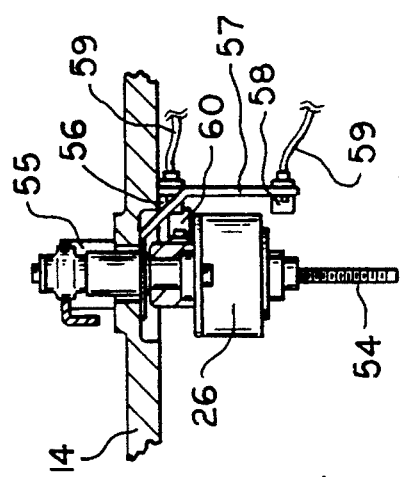

JOYSTICK FOR AN OPHTHALMIC INSTRUMENT WHERE VERTICAL MOVEMENT IS CONTROLLED BY ROTATING THE JOYSTICK

BACKGROUND OF THE INVENTION

1. Field of the Invention

The present invention relates to an improved joystick used for three-dimensional ophthalmic instrument alignment, and more particularly, to a joystick requiring minimal rotational motion.

2. Description of the Prior Art

Many ophthalmic instruments require alignment of a test axis with the center of a patient's eye and an element of the instrument to be spaced a chosen distance from the eye. One such instrument, the non-contact tonometer, has been used by practitioners in their ophthalmic practice for more than 20 years.

The early non-contact tonometers, manufactured by American Optical Corporation, used a joystick, a handle extending from a ball mounted to provide pivotal motion about the center of the ball, in order to move the instrument in a horizontal (X-Z) plane. To move the test axis horizontally in the X direction toward the center of the patient's eye, the joystick is tilted in a corresponding direction. To move the element in the Z direction toward or away from the eye, the joystick is tilted in a corresponding direction. Obviously, compound horizontal movement can be obtained by moving the joystick in a direction between the aforementioned orthogonal directions.

Vertical Y-axis motion in these earlier non-contact tonometers was provided by a separate knob linked by a belt to a threaded shaft mounted for rotation on the carrier and engaging a nut on the support to provide the vertical movement of the test axis. The "firing" button used to actuate the air puff of the early non-contact tonometers was located in the center of the knob used to control vertical, Y-axis, movement.

Later models of the non-contact tonometers produced by Reichert-Jung Ophthalmic Instruments (a successor to American Optical Corporation) and Tokyo Optical Company (Topcon) combined the vertical Y-axis control and "firing" button into the joystick. An example of this type of joystick is taught by Japanese Publication No. 4-50562. Such controls have several disadvantages as taught by the above-mentioned Japanese publication. One problem encountered resulted from twisting the wires used to connect the "firing" button to the instrument electronics and the expense associated with eliminating the twisted wire problem. Another disadvantage of rotating the joystick to control vertical motion was that the practitioner could not accomplish vertical motion when grasping the joystick in the conventional manner because the vertical motion frequently required one or more revolutions of the joystick in order to vertically position the test axis in the center of the eye. Also, many practitioners encounter difficulty in maintaining a horizontal location while adjusting the vertical location of the instrument.

One system for determining the position of a test axis in relation to the center of the eye, as well as the distance of an element from the eye, is taught in commonly owned U.S. Pat. No. 4,881,807. This patent discloses an optical alignment system having a visual display for indicating the relative position of the test axis, and teaches using a joystick for manually positioning the test axis or using three electric motors controlled by information obtained from the optical alignment system to automatically position the instrument.

SUMMARY OF THE INVENTION

An optical instrument includes a manually controlled ball-mounted lever, or joystick, for positioning optical means of the instrument, including a test axis, relative to an eye of a patient. The optical means is fixed to a vertically movable support, which in turn is carried by a horizontally movable carrier. The joystick mechanically moves the carrier in a horizontal plane relative to a frame to center the test axis and space the optical means a proper distance from the eye.

The joystick is connected to a motor drive having an elevation motor for moving the support and optical means in either vertical direction. An actuator extends from the joystick and is arranged to alternately engage a pair of switches connected to the motor drive, such that activation of the elevation motor and its direction of rotation can be controlled with minimal rotational movement of the joystick about its longitudinal axis. Thus, the practitioner can now grasp the joystick in a conventional manner and is not required to change his grip in order to achieve vertical movement of the test axis during the alignment process.

BRIEF DESCRIPTION OF THE DRAWINGS

The nature and mode of operation of the present invention will now be more fully described in the following detailed description of the preferred embodiments taken with the accompanying drawing figures, in which:

FIG. 2 is a top plan view of a joystick and switch means of the present invention;

FIG. 3 is a sectional view taken generally along the line 3—3 in FIG. 2;

FIG. 4 is a side sectional view of an elevation motor and associated elevation limit detector of the present invention;

DETAILED DESCRIPTION

Figure 1:
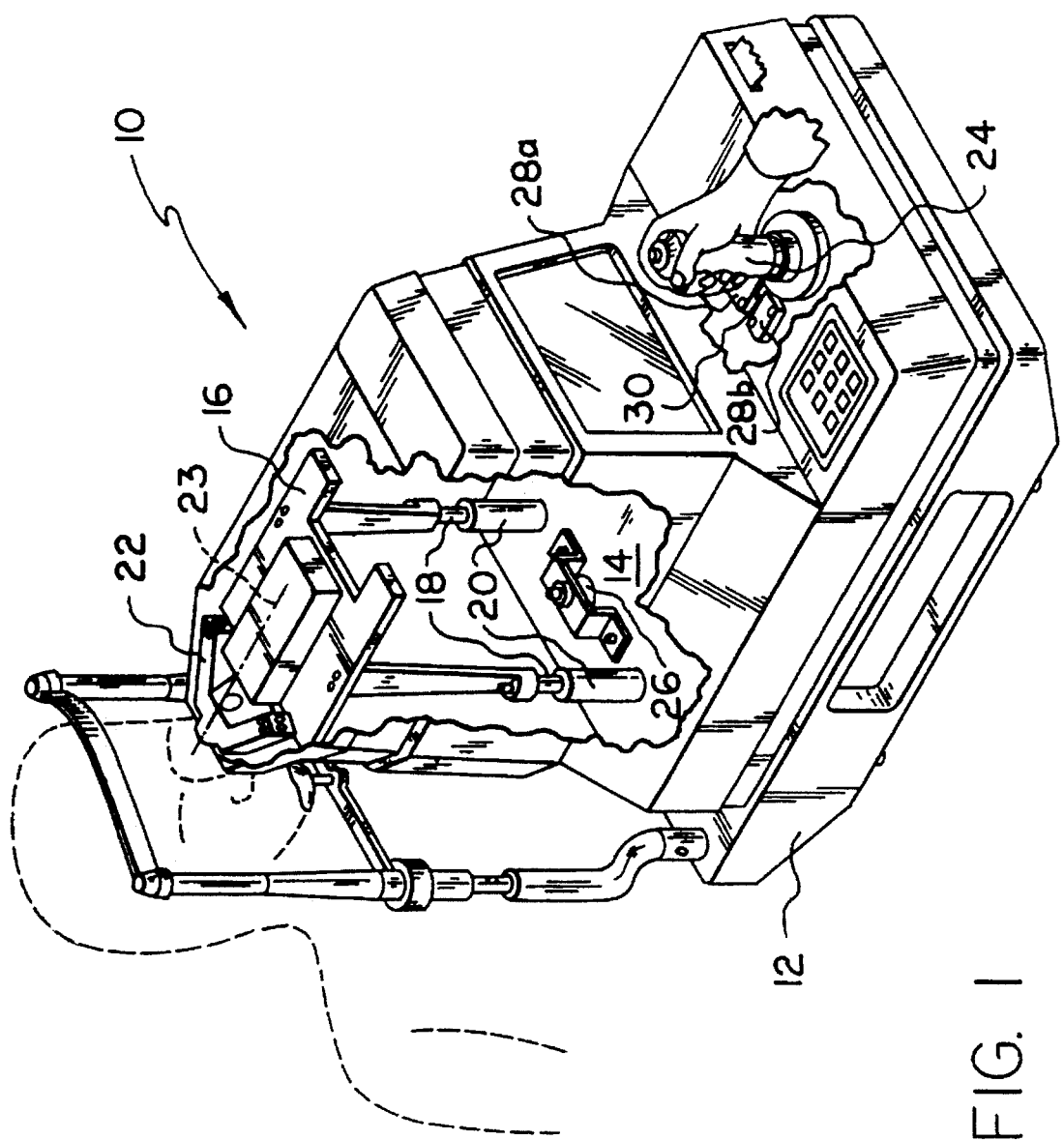
FIG. 1 is a perspective view of an improved ophthalmic instrument formed in accordance with the present invention.

An improved ophthalmic instrument in the form of a non-contact tonometer (NCT) is shown in FIG. 1 and generally designated as 10. NCT 10 is conventional in that it includes a frame 12 having a horizontally movable carrier 14, a support 16 having shafts 18 slidably mounted by carrier tubes 20 for movement of the support vertically relative to carrier 14 and horizontally with the carrier, optical means 22 fixed to support 16 for testing an eye of a patient centered along a test axis 23 of the optical means, and a joystick 24 for controlling movement of optical means 22 in three dimensions. NCT 10 is preferably equipped with an optical alignment system of a type disclosed in commonly owned U.S. Pat. No. 4,881,807.

In accordance with the present invention, an elevation motor 26 is provided to automate upward and downward vertical motion of support 16 and optical means 22 in response to an up switch 28a and a down switch 28b alternately triggered by an actuator 30. Actuator 30 extends radially from joystick 24 and triggers switch means 28a, 28b incident to minimal rotation of the joystick in either direction about its longitudinal axis, thereby facilitating vertical positioning of test axis 23 relative to the eye.

Figure 6:
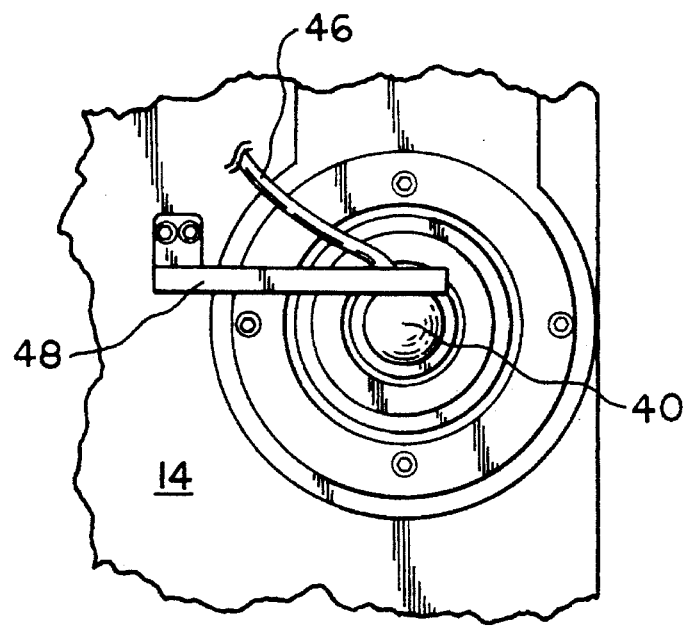
FIG. 6 is a bottom plan view of the joystick.

As best seen in FIGS. 2, 3, and 6, joystick 24 is generally conventional in structure except for actuator 30. Joystick 24 includes a handle portion 31 and is mounted in a known manner on carrier 14 by a teflon ball 32 received within a complementary socket 34 and having slot means 36 for accommodating a set screw 38 which permits coupled rotation of the joystick and socket about the longitudinal axis of the joystick in addition to tilting motion of the joystick within the socket. Joystick 24 also includes a rounded teflon foot 40 arranged to engage a smooth platform 42 fixed to frame 12 throughout the range of motion of carrier 14, and firing switch means 44 connected to a lead 46 for activating optical means 22. As depicted in FIG. only, a retainer arm 48 is fixed to an underside of carrier 14 to underengage platform 42 incident to lifting motion exerted on joystick 24.

Actuator 30 is fixed to socket 34 to extend radially outward from joystick 24 between switches 28a, 28b in a reference rotational position, such that it operatively engages a switch bumper 50a to activate up switch 28a incident to slight rotation of joystick 24 in a clockwise direction and it operatively engages a switch bumper 50b to activate down switch 28b incident to slight rotation of joystick 24 in a counterclockwise direction. Switches 28a, 28b are preferably normally open switches of the general type known as "micro" switches. Obviously, other similar switches are possible.

Switches 28a, 28b are connected by leads 51 to suitable motor control electronics (not shown), preferably of a type disclosed in commonly owned copending U.S. Pat. No. Application entitled "Joystick Override Control" having attorney docket number B6724.

Figure 5:
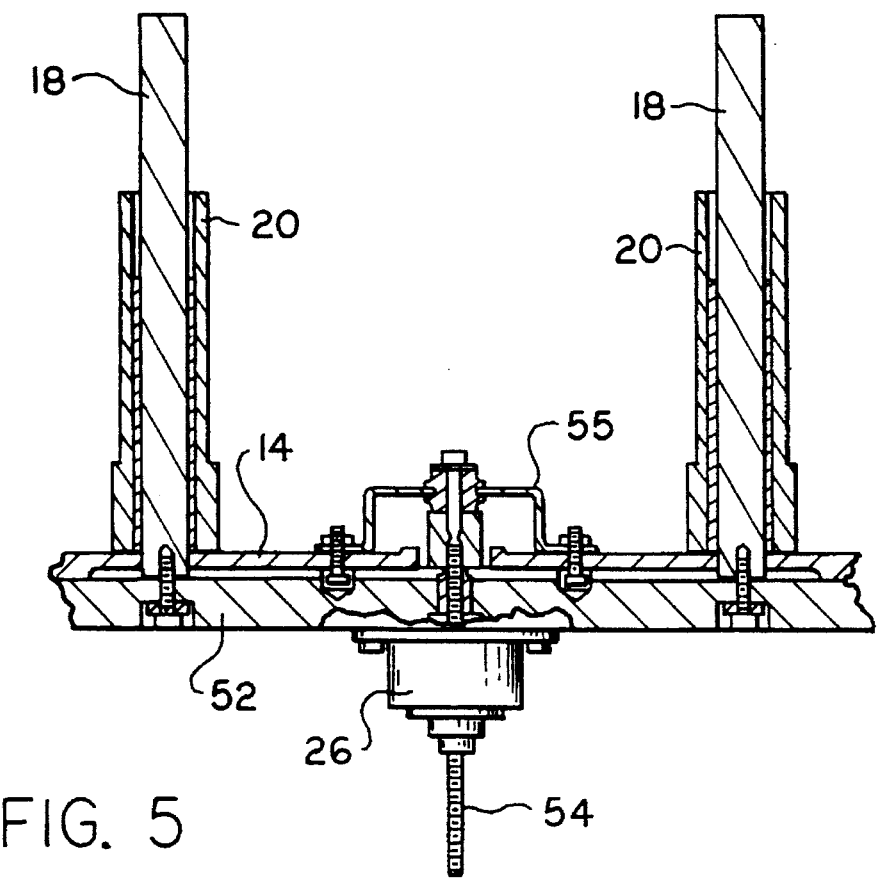
FIG. 5 is a sectional view taken generally along the line 5—5 in FIG. 2.

Referring now to FIGS. 2, 4, and 5, elevation motor 26 is fixed to a lower member 52 of support 16 and includes an internally threaded rotor (not shown) for mating with a threaded rod 54 having an upper portion fixed to carrier 14 by a mounting bracket 55 and a lower portion extending downwardly through carrier 14 and lower member 52. A suitable motor for use in practicing the present invention is a 12 Volt DC, 4.6 Watt bi-directional stepper motor No. 36343-12 available from Haydon Switch and Instrument, Inc. An upper limit switch 56 and a lower limit switch 58 are mounted on a brace 57 and connected to the motor control electronics by leads 59, and a tab 60 is fixed for travel with lower member 52 to interrupt light sensors on upper limit switch 56 upon reaching an uppermost travel limit and lower limit switch 58 upon reaching a lowermost travel limit, thereby causing the respective limit switch to send a signal to the motor control electronics to disable elevation motor 26 when either travel limit is reached. A preferred limit switch is optical transmissive switch model number HOA 1881-11 manufactured by Honeywell.

As may be appreciated from the above description, NCT 10 is significantly easier to operate than prior art ophthalmic instruments, particularly with respect to vertical positioning of test axis 23. To raise test axis 23, an operator merely rotates joystick 24 clockwise through a minimal angle until actuator 30 operatively engages switch bumper 50a on switch 28a, thereby causing the internally threaded rotor of elevation motor 26 to rotate in a first direction forcing the motor and support 16 attached thereto to travel upward along threaded rod 54. Depending on the type of switch 28a, upward travel of optical means 22 may be halted either by returning the joystick to its original reference position away from engagement with switch bumper 50a, or by repeating a "rotate and return" cycle used to commence upward motion. Downward positioning of test axis 23 is commenced in a similar but opposite manner by rotating joystick 24 counterclockwise from its reference position until actuator 30 operatively engages switch bumper 50b. Thus, the present invention allows an operator to move optical means 22 and test axis 23 through their entire range of vertical travel with slight wrist movement and without changing grip on the joystick.

While the present invention is directed to switch-activated motorized movement in opposite vertical (Y) directions, motorized movement in all three dimensions has been described previously, for instance in aforementioned U.S. Pat. No. 4,881,807 at column 6, lines 31–44 and FIG. 7, and thus it is contemplated to provide similar switch means for motorized movement in the horizontal X and Z directions.

What is claimed is:

1. An improved ophthalmic instrument having optical means for testing an eye of a patient comprising: a frame; a support for said optical means connected to said frame; a motor for moving said support in either vertical direction, said motor being responsive to a switch means; lever means for controlling movement of said support in three dimensions, said lever means being tilted for horizontal movement of said support and rotated for vertical movement of said support; and an actuator connected to said lever means and being positioned to operatively engage said switch means upon rotation of said lever in either direction, whereby vertical movement is controlled by rotation of said lever and is independent of the amount of rotation.

2. The improved ophthalmic instrument of claim 1, wherein said actuator is a member extending from said lever means and said switch means includes two switches positioned on opposite sides of said actuator, one of said two switches running said motor in one direction and the other of said two switches running said motor in the other direction.

3. The improved ophthalmic instrument of claim 2, further including a carrier, said support being slidably connected to said carrier for movement in a vertical direction and said carrier being slidably connected to said frame for movement in a horizontal plane.

4. The improved ophthalmic instrument of claim 3, wherein a threaded shaft extends vertically from said carrier, said motor is connected to said support and has an internally threaded rotor operatively engaging said shaft.

5. The improved ophthalmic instrument of claim 3, wherein said lever means includes a ball, a socket for mounting said lever means to said carrier, said ball being universally movable in said socket, a handle extending from said ball, and a foot portion extending from said ball opposite said handle, and said frame includes a horizontal platform frictionally engaging said foot portion.

6. The improved ophthalmic instrument of claim 4, wherein said lever means includes a ball, a socket for mounting said lever means to said carrier, said ball being universally movable in said socket, a handle extending from said ball, and a foot portion extending from said ball opposite said handle, and said frame includes a horizontal platform frictionally engaging said foot portion.

7. The improved ophthalmic instrument of claim 6, wherein said foot portion has a spherical segment surface.

8. The improved ophthalmic instrument of claim 6, further including switch means in said handle for initiating a test by said instrument.

\* \* \* \* \*